US00PP28558P2

(12) United States Plant Patent
Shishido

(10) Patent No.: US PP28,558 P2
(45) Date of Patent: Oct. 24, 2017

(54) ***DIANTHUS* PLANT NAMED 'HOLKAHORISCARLET'**

(50) Latin Name: *Dianthus superbus*
Varietal Denomination: Holkahoriscarlet

(71) Applicant: Kazuyuki Shishido, Chiba (JP)

(72) Inventor: Kazuyuki Shishido, Chiba (JP)

( * ) Notice: Subject to any disclaimer, the term of this patent is extended or adjusted under 35 U.S.C. 154(b) by 0 days.

(21) Appl. No.: 14/999,643

(22) Filed: Jun. 8, 2016

(51) Int. Cl.
*A01H 5/02* (2006.01)

(52) U.S. Cl.
USPC ..... Plt./273

(58) Field of Classification Search
USPC ..... Plt./273
See application file for complete search history.

*Primary Examiner* — Annette Para
(74) *Attorney, Agent, or Firm* — C. A. Whealy

(57) ABSTRACT

A new and distinct cultivar of *Dianthus* plant named 'Holkahoriscarlet', characterized by its compact, uniformly mounding and upright to broadly spreading plant habit; relatively small leaves; freely flowering habit; intense scarlet-colored single flowers; and good container and garden performance.

1 Drawing Sheet

Botanical designation: *Dianthus superbus*.
Cultivar denomination: 'HOLKAHORISCARLET'.

CROSS-REFERENCED TO CLOSELY-RELATED APPLICATIONS

Applicant: Kazuyuki Shishido
Title: *Dianthus* Plant Named 'Holkahoripink'
Plant patent application Ser. No. 14/999,641

BACKGROUND OF THE INVENTION

The present invention relates to a new and distinct cultivar of *Dianthus* plant, botanically known as *Dianthus superbus*, grown commercially as a container and garden plant and hereinafter referred to by the name 'Holkahoriscarlet'.

The new *Dianthus* plant is a product of a planned breeding program conducted by the Inventor in Yokoshibahikari, Sanbu, Chiba, Japan. The objective of the breeding program is to create new container *Dianthus* plants with numerous attractive flowers.

The new *Dianthus* is a naturally-occurring whole plant mutation of *Dianthus superbus* 'Holkahori', not patented. The new *Dianthus* plant was discovered and selected by the Inventor as a single flowering plant from a population of plants of 'Holkahori' in a controlled greenhouse environment in Yokoshibahikari, Sanbu, Chiba, Japan on Aug. 19, 2013.

Asexual reproduction of the new *Dianthus* plant by terminal cuttings propagated in a controlled greenhouse environment in Yokoshibahikari, Sanbu, Chiba, Japan since November, 2013 has shown that the unique features of this new *Dianthus* plant are stable and reproduced true to type in successive generations of asexual reproduction.

SUMMARY OF THE INVENTION

Plants of the new *Dianthus* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Holkahoriscarlet'. These characteristics in combination distinguish 'Holkahoriscarlet' as a new and distinct *Dianthus* plant:

1. Compact, uniformly mounding and upright to broadly spreading plant habit.
2. Relatively small leaves.
3. Freely flowering habit.
4. Intense scarlet-colored single flowers.
5. Good container and garden performance.

Plants of the new *Dianthus* differ primarily from plants of the mutation parent, 'Holkahori', in flower color as plants of 'Holkahori' have dark pink-colored flowers.

Plants of the new *Dianthus* can be compared to Dianthus superbus 'Holkahoripink', disclosed in a U.S. Plant patent application Ser. No. 14/999,641. Plants of the new *Dianthus* differ primarily from plants of 'Holkahoripink', in flower color as plants of 'Holkahoripink' have pink-colored flowers.

Plants of the new *Dianthus* can also be compared to plants of *Dianthus caryophyllus* 'Hilbeakate', disclosed in U.S. Plant Pat. No. 28,023. In side-by-side comparisons, plants of the new *Dianthus* differ primarily from plants of 'Hilbeakate' in the following characteristics:

1. Plants of the new *Dianthus* flower earlier than plants of 'Hilbeakate'.
2. Plants of the new *Dianthus* have slightly larger flowers than plants of 'Hilbeakate'.
3. Plants of the new *Dianthus* and 'Hilbeakate' differ in flower color as plants of 'Hilbeakate' have dark pink-colored flowers.

BRIEF DESCRIPTION OF THE PHOTOGRAPH

The accompanying photograph illustrates the overall appearance of the new *Dianthus* plant showing the colors as true as it is reasonably possible to obtain in colored reproductions of this type. Colors in the photograph may differ slightly from the color values cited in the detailed botanical description which accurately describe the colors of the new *Dianthus* plant. The photograph comprises a side perspective view of a typical flowering plant of 'Holkahoriscarlet' grown in a container.

DETAILED BOTANICAL DESCRIPTION

Plants used in the aforementioned photograph and following observations and measurements were grown during the late winter and early spring in 10.5-cm containers in a glass-covered greenhouse in De Kwakel, The Netherlands and under cultural practices typical of commercial container *Dianthus* production. During the production of the plants, day temperatures ranged from 12° C. to 15° C., night temperatures averaged 12° C. and light levels averaged 7,000 lux. Plants used for the photograph and description were three months old. In the following description, color references are made to The Royal Horticultural Society Colour Chart, 2015 Edition, except where general terms of ordinary dictionary significance are used.

Botanical classification: *Dianthus superbus* 'Holkahoriscarlet'.

Parentage: Naturally-occurring whole plant mutation of *Dianthus superbus* 'Holkahori', not patented.

Propagation:

*Type*.—By terminal cuttings.

*Time to initiate roots, summer*.—About six days at temperatures ranging from 20° C. to 25° C.

*Time to initiate roots, winter*.—About eight days at temperatures about 18° C.

*Time to produce a rooted young plant, summer*.—About three weeks at temperatures ranging from 20° C. to 25° C.

*Time to produce a rooted young plant, winter*.—About five weeks at temperatures about 18° C.

*Root description*.—Medium in thickness, fibrous; whitish in color.

*Rooting habit*.—Moderate branching; medium density.

Plant description:

*Plant and growth habit*.—Herbaceous perennial, typically grown as a container plant; compact, uniformly mounding, upright to broadly spreading plant habit; growth habit, moderate to low vigor.

*Plant height, soil level to top of foliar plane*.—About 6.8 cm.

*Plant height, soil level to top of floral plane*.—About 12.7 cm.

*Plant diameter or spread*.—About 17.8 cm.

*Lateral branches*.—Branching habit: Freely branching habit with about eight main (basal) stems; each main stem with about nine lateral branches. Length: About 3.4 cm. Diameter: About 1.5 mm. Internode length: About 3 mm. Strength: Strong. Aspect: Upright to about 90° from vertical. Texture and luster: Smooth, glabrous; moderately glossy. Color, developing: Close to 142C; at internodes, close to 152B to 152C. Color, developed: Close to 152B to 152C.

Leaf description:

*Arrangement*.—Opposite, simple; sessile.

*Length*.—About 3.5 cm.

*Width*.—About 4 mm.

*Shape*.—Narrowly oblanceolate; slightly carinate.

*Apex*.—Acute.

*Base*.—Attenuate; decurrent.

*Margin*.—Entire.

*Texture and luster, upper and lower surfaces*.—Smooth, glabrous; matte.

*Venation pattern*.—Parallel.

*Color*.—Developing leaves, upper surface: Close to 143B. Developing leaves, lower surface: Close to 143A. Fully expanded leaves, upper surface: Close to 147A; venation, close to 147A. Fully expanded leaves, lower surface: Close to NN137C; venation, close to 143B to 143C.

Flower description:

*Flower form and flowering habit*.—Single flowers arranged singly or in pairs; freely flowering habit with numerous flowers developing during the flowering season; flowers face mostly upright to outwardly.

*Natural flowering season*.—Flowering is continuous from the spring to late summer in The Netherlands; plants begin flowering about nine to twelve weeks after planting.

*Postproduction longevity*.—Flowers last about ten days on the plant; flowers not persistent.

*Fragrance*.—Moderate to strongly fragrant; clove-like, sweet.

*Flower buds*.—Length: About 1.5 cm. Diameter: About 4 mm. Shape: Oblong. Texture and luster: Smooth, glabrous; matte. Color: Close to 138B tinged with close to 183B; towards the base, tinged with close to 187A; petal apices, close to 183B.

*Flower diameter*.—About 3.7 cm.

*Flower depth*.—About 2.7 cm.

*Petals*.—Quantity and arrangement: Five petals arranged in a single whorl. Length: About 3.4 cm. Width: About 1.7 cm. Shape: Spatulate. Apex: Praemorse; slightly crinkled. Base: Narrowly cuneate. Margin: Entire; slightly undulate. Texture and luster, upper surface: Mostly smooth and glabrous, proximally, sparsely pubescent; slightly velvety; matte. Texture and luster, lower surface: Smooth, glabrous, slightly velvety; matte. Color: When opening, upper surface: Close to between 61B and N66A; at the base, close to 145C to 145D. When opening, lower surface: Close to 60D; at the base, close to 145C to 145D. Fully opened, upper surface: Close to 61A to 61B; at the base, close to 145D; with development, color becoming closer between 61A and 64A and towards the base, close to 145D; venation, similar to lamina. Fully opened, lower surface: Close to 64B; at the base, close to 145D; with development, color becoming closer to 70B and towards the base, close to 145D; venation, similar to lamina. Petaloids: Petaloid development has not been observed on plants of the new *Dianthus*.

*Sepals*.—Quantity and arrangement: Five sepals arranged in a single whorl; proximal 24% portion of the sepals are fused into a campanulate-shaped calyx. Calyx length: About 1.7 cm. Calyx diameter: About 5 mm. Sepal length: About 1.7 cm. Sepal width, at base of "free" portion: About 3 mm. Shape: Narrowly oblong. Apex: Acute. Margin: Entire. Texture and luster, upper surface: Smooth, glabrous; glossy. Texture and luster, lower surface: Smooth, glabrous; matte. Color: When opening, upper surface: Close to 144A to 144B. When opening, lower surface: Close to 138B; towards the apex, close to 187A. Fully opened, upper surface: Close to 144B. Fully opened, lower surface: Close to 143B; towards the apex, close to 187B.

*Peduncles*.—Length: About 2.6 cm. Diameter: About 1 mm. Strength: Moderately strong. Aspect: About 15° from the stem axis. Texture and luster: Smooth, glabrous; moderately glossy. Color: Close to NN137C.

*Reproductive organs*.—Stamens: Quantity: About ten stamens per flower. Filament length: About 1.7 cm. Filament color: Close to NN155D. Anther length: About 2 mm. Anther shape: Oblong. Anther color: Close to 159D. Pollen: Scarce. Pollen color: Close to 156D. Pistils: Quantity: About two per flower. Pistil length: About 1.4 cm. Stigma diameter: About 1.75 mm. Stigma shape: Pointed, spirally curved. Stigma color: Close to 72B. Style length: About 1.2 cm. Style color: Close to NN155D. Ovary color: Close to 144A. Fruits and seeds: Fruit and seed development have not been observed on plants of the new *Dianthus*.

Disease & pest resistance: Plants of the new *Dianthus* have not been observed to be resistant to pathogens and pests common to *Dianthus* plants.

Garden performance: Plants of the new *Dianthus* have been observed to have good garden performance and to tolerate wind, rain and high temperatures about 35° C. and to be suitable for USDA Hardiness Zones 5 to 9.

It is claimed:

1. A new and distinct *Dianthus* plant named 'Holkaho-riscarlet' as illustrated and described.

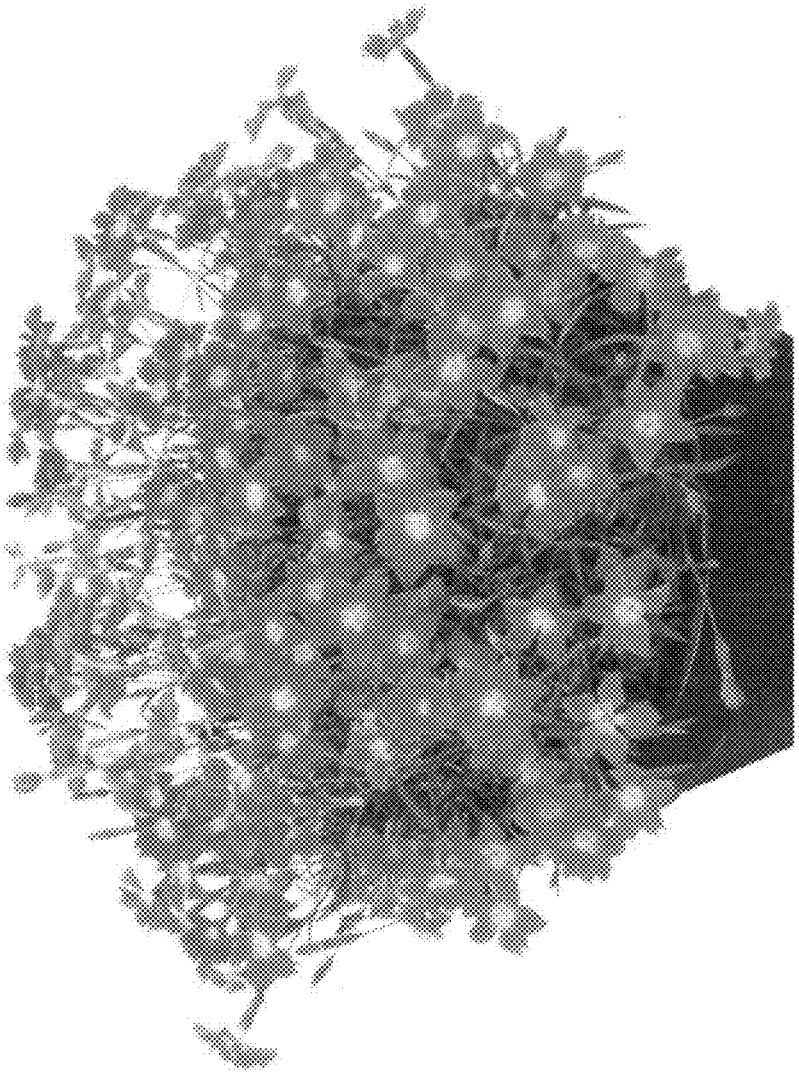

* * * * *